(12) United States Patent
Azik

(10) Patent No.: US 7,291,351 B2
(45) Date of Patent: Nov. 6, 2007

(54) CITRUS-DERIVED COSMETIC AND MEDICINAL COMPOSITION AND ASSOCIATED METHODS

(75) Inventor: Murat Azik, Lakeland, FL (US)

(73) Assignee: FL Dept of Citrus, Lakeland, FL (US)

( * ) Notice: Subject to any disclaimer, the term of this patent is extended or adjusted under 35 U.S.C. 154(b) by 486 days.

(21) Appl. No.: 10/928,950

(22) Filed: Aug. 27, 2004

(65) Prior Publication Data

US 2005/0048145 A1    Mar. 3, 2005

Related U.S. Application Data

(60) Provisional application No. 60/498,219, filed on Aug. 27, 2003.

(51) Int. Cl.
*A01N 65/00* (2006.01)
(52) U.S. Cl. .................................................... 424/736
(58) Field of Classification Search .................... None
See application file for complete search history.

*Primary Examiner*—Christopher R. Tate
*Assistant Examiner*—Deborah A. Davis
(74) *Attorney, Agent, or Firm*—Dennis L. Cook, Esq

(57) ABSTRACT

A method for making a nutritional and medicinal citrus-based cream that is all-natural and highly stable includes the steps of grinding citrus peel into a puree consistency and adding water to the ground citrus peel to form a mixture. The mixture is then pH adjusted to a value in a range of 1.5-4.0. The pH-adjusted mixture is heated at a predetermined temperature for a predetermined time period to achieve a gradual extraction of unwanted compounds such as water-soluble pectins, and the heated mixture is filtered. Water is then added to a filtrate from the filtering step to form a mixture, which is filtered to achieve a cream having a desired consistency. The invention is also intended to encompass the cream composition made by the described method.

1 Claim, No Drawings

CITRUS-DERIVED COSMETIC AND MEDICINAL COMPOSITION AND ASSOCIATED METHODS

CROSS-REFERENCE TO RELATED APPLICATION

The present application claims the benefit of previously filed co-pending Provisional Patent Application, Ser. No. 60/498,219 filed Aug. 27, 2003.

BACKGROUND OF THE INVENTION

1. Field of the Invention

The present invention relates to compositions for cosmetic and medicinal uses, and, more particularly, to such compositions that are made from all-natural ingredients, most particularly, citrus.

2. Description of Related Art

Compounds found primarily in the peel portion of citrus are known to have anti-histamine properties. Grapefruit (*Citrus paradisi*), in particular, has been reported to contain high amounts of these compounds, among which are the bioflavanoids such a naringin, rutin, hesperitin, and quercitin. Although these compounds are found in nature, they are highly concentrated in citrus varieties, especially the grapefruit. There are many compounds in citrus that work in concert with the bioflavanoids; so this is not limited to the action of the bioflavanoids alone. The activity of the bioflavanoids and histamine is detailed in E. Middleton and G. Drzewiecki (Biochem. Pharmacol. 33(21), 3333, 1984); N. S. Parmar (Int. J. Tissue React. 5(4), 415, 1983); and I. Lambey et al. (Acta Physiol. Pharmacol. Bulg. 6(2), 70, 1980).

Cream bases are used in a wide variety of cosmetic and medicinal compositions. Such cream bases have mainly included aloe, lanolin, or non-biological carriers such as petroleum. Lanolin has been found to be an allergen in a large segment of the population, and aloe alone has not been successfully used to make cream bases. Petroleum carriers are often avoided, since current market demand includes a desire for more all-natural products.

Psoriasis is a damaging skin disease that also affects the scalp in the form of dandruff, with approximately 3% of all Americans suffering from this painful and embarrassing disease. Research by the National Psoriasis Foundation has indicated that psoriasis can be treated by a combination of psoralen and ultraviolet light.

Thus, what is needed is an all-natural creamy base raw ingredient that has medicinal and nutritional properties that can be used as a base for cosmetics and as a thickener or filler for food products.

SUMMARY OF THE INVENTION

The present invention addresses the need for an all-natural cream base that has medicinal properties in and of itself and also can serve as a base for cosmetics such as moisturizers or as a nutritional creamy raw material for use as a filler or thickening material for food products.

The method of the present invention is for making such a citrus-based cream that is all-natural and highly stable. The method comprises the steps of grinding citrus peel into a puree consistency and adding water to the ground citrus peel to form a mixture. The mixture is then pH adjusted to a value in a range of 1.5-4.0. The pH-adjusted mixture is heated at a predetermined temperature for a predetermined time period to achieve a gradual extraction of such compounds as water-soluble pectins, and the heated mixture is filtered. Water is then added to a filtrate from the filtering step to form a mixture, which is filtered to achieve a cream having a desired consistency.

The invention is also intended to encompass the cream composition, which comprises a nutritional, natural raw material for use as a medicinal and cosmetic cream base composition or food product thickener or filler. The cream base comprises pureed citrus fruit peel having been pH-adjusted to a range of 1.5-4.0, diluted with water, heated for a sufficient time and to a sufficient temperature to substantially remove the water-soluble pectins and filtered to a desired consistency.

Grapefruit is preferred for the production of this cream because of its high concentration of active compounds. It should be noted, however, that this treatment may be utilized with all forms of citrus and is not intended to be limited to grapefruit. Different varieties of citrus can be used separately or in a mixture to achieve an inventive result. The active components of citrus for this treatment are numerous and are believed to work in concert to achieve the desired result. The compounds are found in high concentration in the peel portion of the fruit but may be found in the juice and seed portions as well.

The compounds found in grapefruit work to treat psoriasis, and the cream of the present invention is therefore useful in such applications wherein psoralens provide relief. In addition, the cream is useful to treat dandruff, skin cell carcinoma, and acne; to prevent insect bites; and to form a base for a wide range of cosmetics, including as a moisturizer, shampoo, and scalp treatment.

The creamy material may also be used as a raw ingredient, filler, or thickening material for food products.

The features that characterize the invention, both as to organization and method of operation, together with further objects and advantages thereof, will be better understood from the following description.

DETAILED DESCRIPTION OF THE PREFERRED EMBODIMENTS

A description of the preferred embodiments of the present invention will now be presented.

The method of the present invention is for making a citrus-based cream that is all-natural and highly stable. The method comprises the steps of squeezing grapefruit via cold-pressing, and collecting the peel. The citrus peel is ground into a puree consistency, for example, by using an industrial meat/food grinder in combination with an industrial recirculating food processor. An exemplary embodiment of this step comprises grinding the peel in one pass through a Hobart model meat grinder at 1725 rpm, and then processed with ten passes through a Comitrol processor, model 1700, with a 180084-2 micro-cut head at 9391 rpm.

Water is added to the ground citrus peel to form a mixture that is easy to work with, in a range from 1:1 to 100:1 water:peel puree, most preferably 10:1.

The mixture is then blended thoroughly, for example, using a Waring model commercial blender for 3 min at high speed. Depending on the beginning material the mixture can be stirred, allowed to settle, filtered, and mixed with water one or several times then blended to obtain the desired consistency. The pH is then adjusted to a value in a range of 1.5-4.0, most preferably 1.5, using, for example, concentrated nitric acid or other acids preferred for food use such as citric acid. The pH-adjusted mixture is heated at a predetermined temperature for a predetermined time period to achieve a gradual extraction of unwanted compounds such as water-soluble pectins. The preferred temperature range is approximately 65-85° C., and the preferred time period range is approximately 20 min-4 h. Most preferably these values comprise gradually heating to 75° C. for 30 min, and then maintaining the mixture at that temperature for an additional 30 min.

The hot mixture is then filtered through a fine cloth filter, such as Miracloth, until excess water is removed. Water is then added to a filtrate from the filtering step to form a mixture that is easy to work with, for example, using the Waring blender for 2 min at high speed. An exemplary dilution ratio comprises 1:1-100:1 water:filtrate, with a preferred ratio of 1:1. An antibacterial such as Sodium Benzoate may be added at a preferred 0.5% solution to prevent bacterial growth.

The diluted filtrate is then again filtered through a fine cloth filter such as Miracloth to remove excess water and to achieve a cream having a desired consistency. In addition, the filtrate may also be press filtered to achieve the desired consistency.

It may be appreciated by one skilled in the art that additional embodiments may be contemplated, including the use of citrus fruits other than grapefruit, and similar ranges of temperature and pH to achieve substantially the same result.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the method described herein are by way of example, and the scope of the invention is not limited to the exact method steps outlined herein.

What is claimed is:

1. A method for making a 100% citrus based composition comprising the steps of:
    grinding cold pressed citrus peel into a puree consistency;
    adding deionized water to the ground citrus peel puree to make a mixture;
    blending the ground citrus peel/water mixture;
    stirring the blended mixture and allowing precipitates and/or non-soluble material to settle;
    removing the top portion of the blended mixture by decanting;
    filtering the blended mixture;
    repeating the decanting and filtering steps one or more times;
    adjusting the filtered mixture with acid to achieve approximately 1.5 pH;
    heating the pH-adjusted mixture for a predetermined time period for approximately one hour to achieve a pH-adjusted mixture temperature of between 65-85 degrees C.;
    filtering the heated mixture to remove excess free moisture;
    adding water to the filtered mixture to form a new mixture; and,
    filtering the new mixture and blending the new mixture to achieve a desired creamy consistency.

* * * * *